United States Patent [19]

Horn et al.

[11] 4,288,392

[45] Sep. 8, 1981

[54] PROCESS FOR THE PREPARATION OF DIALKYL PHOSPHORIC ACIDS

[75] Inventors: James M. Horn, Richmond, Va.; Byron E. Johnston, Skillman, N.J.; Roger P. Napier, Califon, N.J.; Thomas N. Williams, Plainfield, N.J.

[73] Assignee: Mobil Oil Corporation, New York, N.Y.

[21] Appl. No.: 109,371

[22] Filed: Jan. 3, 1980

[51] Int. Cl.$^3$ .............................................. C07F 9/09
[52] U.S. Cl. .................................... 260/983; 260/963
[58] Field of Search ........................................ 260/983

[56] References Cited

U.S. PATENT DOCUMENTS 2,999,085  9/1961  King et al. .......................... 260/983
3,194,827  7/1965  Lutz et al. ........................... 260/983

Primary Examiner—Anton H. Sutto
Attorney, Agent, or Firm—Charles A. Huggett; Michael G. Gilman; Hastings S. Trigg

[57] ABSTRACT

This application is directed to a process for preparing dialkyl phosphoric acid, preferably di(2-ethylhexyl) phosphoric acid. This latter material is used in uranium extraction from wet-process phosphoric acid as a kerosine solution along with a synergist, trioctylphosphine oxide.

5 Claims, No Drawings

PROCESS FOR THE PREPARATION OF DIALKYL PHOSPHORIC ACIDS

BACKGROUND OF THE INVENTION

1. Field of the Invention

This application is directed to a process for preparing dialkyl phosphoric acid, preferably di(2-ethylhexyl) phosphoric acid. This latter material is used in uranium extraction from wet-process phosphoric acid as a kerosine solution along with a synergist, trioctyl phosphine oxide.

2. Description of the Prior Art

Although the individual steps in the process of this invention are generally known, the precise manipulations involved have not been shown in the art, insofar as is now known.

SUMMARY OF THE INVENTION

This invention provides a process to produce dialkyl phosphoric acid that comprises:
(a) reacting $PCl_3$ with $C_1$–$C_{12}$ alkanol in a molar ratio of said alkanol:$PCl_3$ of 3 at 10°–15° C. under an inert gas atmosphere, to produce a mixture of bis-(alkyl) hydrogen phosphite, alkyl chloride, and HCl;
(b) chlorinating said mixture with a stiochiometric amount of chlorine gas at about 20° C., until the reaction mixture attains a yellow-green color and a stable Platinum-Calomel electrode reading is obtained in the range of about 880–910 m.v.; optionally sparging with inert gas at about 50° C. until the HCl content is below about one weight percent, thus producing a solution of dialkyl phosphorochloridate in alkyl chloride;
(c) hydrolyzing said solution with water at 80°–100° C. for about 4–6 hours, using sufficient water to effect a final HCl content below about 11 weight percent, to produce dialkyl phosphoric acid product; and
(d) separating said product.

DESCRIPTION OF SPECIFIC EMBODIMENTS

The alkanol reactant used in the process of this invention is an alcohol having 1–12 carbon atoms, i.e., $C_1$–$C_{12}$ alkanols. Typical alkanols include methanol, ethanol, butanol, isobutanol, octanol, 2-ethylhexanol, decanol, and dodecanol. 2-Ethylhexanol is preferred, because high quality di-(2-ethylhexyl) phosphoric acid is required for modern-day uranium extraction processes. The di(2-ethylhexyl) phosphoric acid produced in accordance with this invention is of such high quality that further purification is not necessary for use as an extractant.

The process of this invention can also be used to produce $diC_1$–$C_{12}$ alkylthio phosphoric acids, as well as the corresponding mixed alkyl, alkylthio phosphoric acids. Also contemplated is the production of mixed alkyl ($C_1$–$C_{12}$) phenyl (including halo, nitro, etc. phenyl) phosphoric acids. In general, the phosphoric acids described above can be used as lubricant additives and have other uses known in the art.

In the following description, the present process is described in terms of the preparation of the preferred di-(2-ethylhexyl) phosphoric acid.

The process of this invention involves three major steps. The first step involves preparation of bis-(2-ethylhexyl) hydrogen phosphite (BEHHP). In the second step, BEHHP is chlorinated to produce di-(2-ethylhexyl) phosphorochloridate (DEHPC) which is hydrolyzed in the third step to produce di-(2-ethylhexyl) phosphoric acid (DEHPA).

In the first step of the process, phosphorus trichloride is reacted with 2-ethylhexanol. An intermediate tri-(2-ethylhexyl) phosphite is produced with the evolution of hydrochloric acid. This intermediate is rapidly dealkylated by the hydrochloric acid to produce the BEHHP, according to the following equation:

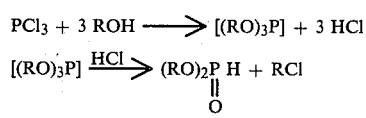

The reaction is carried out using a molar ratio of 2-ethylhexanol to phosphorus trichloride of 3. In this operation, it is essential to maintain the stoichiometry to obtain good final purity and productivity. If too much 2-ethylhexanol is used, it carries over into the next chlorination step where some of it reacts to form tri-(2-ethylhexyl) phosphate. If too little alcohol is used, mono-(2-ethylhexyl) phosphoric acid values in the final product are increased.

The reaction is feasibly carried out by adding exactly 1 mole of phosphorous trichloride to 3 moles 2-ethylhexanol, while maintaining the reaction temperature at 15° C. In view of the fact that tri-(2-ethylhexyl) phosphite can be readily oxidized by air or oxygen to the corresponding phosphate, an undesirable by-product, the reaction should be carried out under an inert gas atmosphere, such as nitrogen, flue gas and the like. The product BEHHP production is monitored by gas phase chromatography (GPC).

The chlorination step is carried out by chlorinating the mixture from the first step, which contains BEHHP, 2-ethylhexyl chloride, and hydrogen chloride, using a molar amount of chlorine, based upon the BEHHP content. This reaction is carried out by adding the chlorine over a 2–3 hour period at 20° C.

The chlorination step is complete when
1. the mixture in the reactor attains a yellow-green color
2. a molar amount of chlorine has been added
3. GPC shows 98+% conversion
4. a stable Platinum-Calomel electrode reading in the range of about 880–910 m.v. is attained.

On completion of the reaction, the reaction mixture is then optionally sparged with nitrogen at 25° C. until HCl concentration measures less than 1 wt. %.

The final major step in the process of this invention is the hydrolysis of the di-(2-ethylhexyl) phosphorochloridate to product DEHPA. This reaction is carried out using an excess amount of water over the stoichiometric amount. Dealkylation of the DEHPA to mono-(2-ethylhexyl) phosphoric acid by HCl at elevated temperatures is a side reaction that must be controlled to produce acceptable product. This dealkylation is minimized by adjusting the amount of water so that a final HCl content below about 11 wt. % is obtained. In general, the hydrolysis reaction is carried out at 80°–100° C. Considerable amounts (above 60 wt. %) of tetra-(2-ethylhexyl) pyrophosphate are formed in this process from the reaction of DEHPC with DEHPA. This lowers product purity and causes processing problems, such as poorer phase separation. This is overcome by extending the hydrolysis time to 4–6 hours to hydrolyze the pyrophosphate to DEHPA product. An alternative and preferred method to carry out the hydrolysis is to hydrolyze the mixture, as above described for about 2 hours at about 80° C. Then the aqueous layer containing the HCl is separated. A second hydrolysis, using the same amount of water as previously stated, is carried out at 95°–100° C. for about 3 hours.

The reaction mixture from the hydrolysis consists of an upper organic layer DEHPA product dissolved in 2-ethylhexyl chloride and a lower aqueous layer. The presence of the 2-ethylhexyl chloride increases the density difference between DEHPA and the aqueous phase, thus improving phase separation. Although phase separation could be carried out at about room temperature, it is preferred to carry out phase separation at 70°–80° C. for maximum efficiency and process considerations.

In order to obtain the final product, residual water and 2-ethylhexyl chloride by-product must be removed. This can be accomplished by various means including vacuum distillation and sparging with an inert gas such as nitrogen. In view of the fact that the DEHPA product begins to degrade at temperatures of about 150° C., there is a temperature limitation upon the vacuum stripping. In practice, the bulk of the 2-ethylhexyl chloride can be removed by stripping to 125°–130° C. at 50 mm. mercury. The residual chloride content can then be reduced below 2 wt. % by inert gas sparging, e.g., 0.37 pounds/$N_2$/hour/pound DEHPA for 1–2 hours at about 125° C.

An alternate and preferred procedure for 2-ethylhexyl chloride removal would be to use a wiped film evaporator in place of the nitrogen sparging step. It has been found that essentially complete 2-ethylhexyl chloride removal can be obtained at about 150° C. and 2 mm. mercury pressure over a broad range of feed rates without product degradation or color buildup. Results of wiped film evaporator testing are set forth in the following table.

TABLE 1

WIPED FILM EVAPORATOR TEST

| Sample | Feed Rate (Pounds/Hr)[2] | % DEHPA (By Titration) | % MEHPA (By Titration) | % EHCl (By TGA) |
|---|---|---|---|---|
| Feed[1] | — | 90.0 | 2.0 | 6.0 |
| R-1 | 112 | 95.7 | 2.1 | 0.2 |
| R-2 | 160 | 95.7 | 2.2 | 0.2 |
| R-3 | 227 | 96.2 | 2.1 | 0.2 |
| R-4 | 223 | 96.0 | 2.1 | 0.2 |
| R-5 | 335 | 95.9 | 2.1 | 0.2 |
| R-6 | 478 | 95.9 | 2.1 | 0.2 |
| R-7 | 274 | 96.6 | 1.9 | 0.2 |
| R-8 | 415 | 96.4 | 1.9 | 0.2 |
| R-9 | 538 | 95.7 | 2.1 | 0.2 |
| R-10 | 694 | 95.7 | 2.0 | 0.2 |
| R-11 | 909 | 95.7 | 2.1 | 0.2 |
| R-12 | 981 | 95.8 | 2.0 | 0.2 |

[1]Feed was a synthetic blend of commercial DEHPA (93.6% DEHPA, 1.9% MEHPA) and enough Ethylhexyl Chloride added to produce a material containing 6% Ethylhexyl Chloride
[2]Test conditions were 2 mm Hg and 150° C. using a Pfaudler wiped film evaporator (4.1 square foot surface area).

A typical pilot plant run which illustrates the process of this invention is described in the following example.

EXAMPLE

There was charged 121.2 lbs. of 2-ethylhexanol to a reaction vessel using a nitrogen blanket. Agitation was commenced and the reactor was cooled to 10°–15° C. About 42.61 lbs. $PCl_3$ were charged to a holding tank and the $PCl_3$ was introduced into the reactor at a rate of 28.4 lbs per hour while maintaining the temperature at 10°–15° C.

Then the reactor contents were pumped around a loop for testing and observation, and refrigeration was continued. Also activated was a millivolt meter connected with a Platinum-Calomel electrode inserted into the reaction mixture. Chlorine gas was introduced at a rate of about 7.33 lbs. per hour. At the chlorination end point, the chlorine total addition was about 21.99 lbs. and a yellow-green color appeared. The millivolt reading had increased to about 905–910. At this point, the reactor contents was sparged with nitrogen at a rate of 3.5 lbs. per hour and the reactor contents were warmed to 50° C. At this temperature, sparging was continued until the HCl level in the chloridate product was 1% or less (about 4 hours). Water (119 lbs.) was charged to the reactor and the reactor contents were heated to 80° C. and held at that temperature for 2 hours with agitation. Agitation was stopped and the phases were permitted to separate for about 0.5–1 hour. Then the aqueous layer was drained.

An additional 119 lbs. of water were added to the reactor. The reactor was heated to 95°–100° C. and maintained at that temperature for four hours with agitation. Agitation was again stopped, and the phases were allowed to separate for 0.5–1 hour. Then the aqueous layer was drained. Vacuum was applied to a pressure of 10 mm. Hg and the temperature was held at 90°–95° C. for 0.5 hour. The reactor temperature was raised to 125° C. while maintaining 10 mm. mercury pressure and held for 2 hours. 2-Ethylhexyl chloride was condensed and collected in a receiver. Then the reactor contents were sparged with nitrogen at a rate of 3.7 lbs. per hour at 125° C. and 50 mm. mercury, until the 2-ethylhexyl chloride content was below 2 wt. %. Reactor contents were then cooled and discharged through a 100–200 micron cartridge filter.

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

What is claimed is:

1. A process to produce dialkyl phosphoric acid that comprises:

(a) reacting $PCl_3$ with $C_1$–$C_{12}$ alkanol in a molar ratio of said alkanol:$PCl_3$ of 3 at 10°–15° C., under an inert gas atmosphere, to produce a mixture of bis(alkyl) hydrogen phosphite, alkyl chloride, and HCl;

(b) chlorinating said mixture with a stoichiometric amount of chlorine gas at about 20° C., until the reaction mixture attains a yellow-green color and a stable Platinum-Calomel electrode reading is obtained in the range of about 880–910 m.v.; optionally sparging with inert gas at about 50° C. until the HCl content is below about one weight percent, thus producing a solution of dialkyl phosphorochloridate in alkyl chloride;

(c) hydrolyzing said solution with water at 80°–100° C. for about 4–6 hours, using sufficient water to effect a final HCl content below about 11 weight percent, to produce dialkyl phosphoric acid product; and (d) separating said product.

2. The process of claim 1, wherein said $C_1$–$C_{12}$ alkanol is 2-ethylhexanol and said product is di-(2-ethylhexyl) phosphoric acid.

3. The process of claim 1, wherein (c) said hydrolyzing is carried out in two stages with intermediate phase separation.

4. The process of claim 2, wherein (c) said hydrolyzing is carried out in two stages with intermediate phase separation.

5. The process of claim 1, 2, 3, or 4, wherein (d) said product is separated by vacuum distillation and sparging with inert gas.

* * * * *